United States Patent [19]

Zomer

[11] Patent Number: 5,605,812
[45] Date of Patent: Feb. 25, 1997

[54] **TEST KIT AND METHOD FOR THE QUANTITATIVE DETERMINATION OF COLIFORM BACTERIA AND *E. COLI***

[75] Inventor: Eliezer Zomer, Newton, Mass.

[73] Assignee: Charm Sciences, Inc., Malden, Mass.

[21] Appl. No.: 446,039

[22] Filed: May 19, 1995

[51] Int. Cl.⁶ ........................................ C12Q 1/10
[52] U.S. Cl. ................ 435/38; 435/30; 435/34; 435/39; 435/810; 435/975
[58] Field of Search ................... 435/29, 34, 38, 435/39, 7.37, 30, 810, 975

[56] References Cited

U.S. PATENT DOCUMENTS

| | | |
|---|---|---|
| 3,416,998 | 12/1968 | Streitfeld . |
| 3,959,081 | 5/1976 | Witz et al. . |
| 4,072,575 | 2/1978 | Lanham et al. . |
| 4,242,447 | 12/1980 | Findl et al. . |
| 4,340,671 | 7/1982 | Gibson . |
| 4,643,968 | 2/1987 | Weaver . |
| 4,812,393 | 3/1989 | Goswami et al. . |
| 4,812,409 | 3/1989 | Babb et al. . |
| 4,923,804 | 5/1990 | Leu et al. . |
| 4,925,789 | 5/1990 | Edberg . |
| 5,055,414 | 10/1991 | Babb et al. . |
| 5,084,041 | 1/1992 | Oxley et al. ........................ 604/410 |
| 5,108,902 | 4/1992 | Mooberry . |
| 5,108,903 | 4/1992 | Mooberry . |
| 5,164,301 | 11/1992 | Thompson et al. . |
| 5,210,022 | 5/1993 | Roth et al. . |
| 5,223,402 | 6/1993 | Abbas et al. . |
| 5,232,838 | 8/1993 | Nelson et al. . |
| 5,284,772 | 2/1994 | Oxley ........................ 436/47 |
| 5,298,392 | 3/1994 | Atlas et al. . |
| 5,354,661 | 10/1994 | Doyle et al. . |
| 5,372,801 | 12/1994 | Malmros et al. . |
| 5,393,662 | 2/1995 | Roth et al. ........................ 435/38 |
| 5,411,867 | 5/1995 | Chang et al. . |

FOREIGN PATENT DOCUMENTS

WO9523026  8/1995  WIPO .

OTHER PUBLICATIONS

"Fluorocult® LMX–Broth Modified acc. to Manafi and OBner"—New Culture Medium for the Simultaneous Detection of Coliform and *E. Coli*.

*Primary Examiner*—Leslie Wong
*Attorney, Agent, or Firm*—Richard P. Crowley

[57] ABSTRACT

A test kit and method particularly for the quantitative determination of total coliform bacteria and *E. coli* particularly in large volume test samples, such as water, wherein the media includes an agent which changes color and a gelling agent which reacts or provides in situ with the test sample a semi-solid broth or media for incubation, thereby restricting the mobility of the growth bacteria and permitting a quantitative count of the separate, colored bacteria colonies.

47 Claims, 1 Drawing Sheet

SCREEN COLIFORMS:
1. Pour 105 ml water sample into open E*Colite bag.
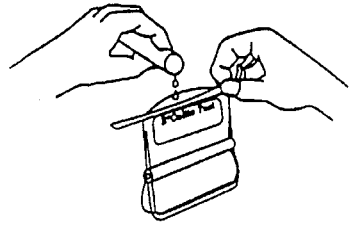
2. Twirl three times to close bag and seal with wire.
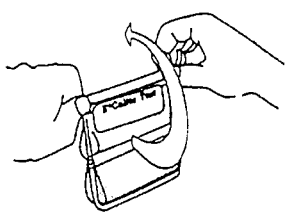
3. Remove clip. Shake to mix medium.
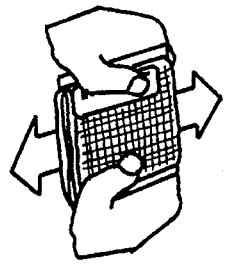
4. Incubate for 16-24 hours at 37°C
5. Observe under long wave UV (366nm) light after 24-48 hours.
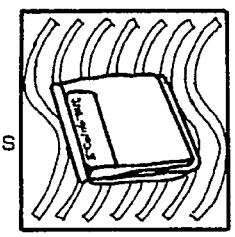
6. Blue fluorescence = E.coli
No fluorescence = other coliforms
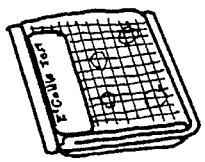
Yellow = No coliforms or E.coli
Green/blue spots = Coliforms present 
CONFIRM E.coli:
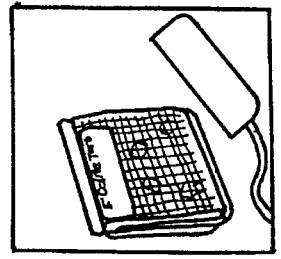

TEST KIT AND METHOD FOR THE QUANTITATIVE DETERMINATION OF COLIFORM BACTERIA AND E. COLI

BACKGROUND OF THE INVENTION

It is widely desirable to provide rapid, effective detection and identification of various and numerous microorganisms in test samples, say for example, from, but not limited to, water, food and body fluids, such as for example, to detect and identify a total coliform bacteria and/or also E. coli bacteria in a particular test sample.

One enzymatic test identification method is known as the MUG test which was designed for the detection of E. coli. This test is well known and is set forth in U.S. Pat. No. 5,223,402, hereby incorporated by reference. The test method is for detecting total coliform bacteria and E. coli and other microbes employing one or more chemiluminescent compounds in an enzymatic test technique. The test is the detection of a qualitative presence or absence of total coliform bacteria or E. coli or other microbes in a sample by combining the sample with a 1-2-dioxetane compound which decomposes to a light-emitting portion with the reaction of at least one hydrolytic enzyme present in the microorganism in the sample, thereby triggering light emission, so that the light emission can then be detected. The test indicates the presence of the hydrolase activity of the particular microbes in the sample on exposing the light-emitting sample to a light-sensitive detector over a period of time.

An improved MUG test method is directed to the simultaneous detection of total coliform bacteria and E. coli in a test sample, for example a water sample, in a test method known as Fluorocult® LMX Broth (a culture medium trademark of BDH Inc. of Brampton, Ontario, Canada). This improved MUG test method is described for example in the paper "Simultaneous Detection of Total Coliforms and E. coli—Fluorocult® LMX Broth" by Dr. Rolf Ossmer et al presented at the 15th International Symposium/FOOD MICRO 1993, The International Committee on Food Microbiology and Hygiene, Aug. 31–Sep. 3, 1993 in Bingen/Rhine, Germany, hereby incorporated by reference.

The improved MUG test provides for a selected enrichment broth which permits the simultaneous detection in the qualitative manner of total coliforms and E. coli in bacterial testing of water, food and other materials. The broth has been formulated to provide a high nutritional quality and phosphate buffers to guarantee a high growth rate for the coliforms present and employs a lauryl sulfate to inhibit to a large extent the growth of gram-positive bacteria. The simultaneous detection of total coliforms and E. coli are made possible by the addition of chromogenic substrates in the broth which permit the easier identification of coliforms due to a color change from a yellow color to a blue-green color about the coliforms. The use of the MUG compound provides more specific identification of E. coli within the test sample. The broth employs a halo-indolyl-β-D-galactopyranoside (X-GAL) which is a 5-bromo-4-chloro-3-indolyl-β-D-galactopyranoside which is cleaved by coliforms producing a blue-green color in the broth after incubation. The visual observation of this blue-green coloration would indicate the presence of total coliform bacteria in the test sample, while the absence thereof indicates the absence of total coliform bacteria to a lower limit.

The broth also employs an amplification agent, such as a thiogalactopyranoside, such as a 1-isopropyl-β-D-1-thiogalactopyranoside (IPTG) for an amplification factor in the enzyme synthesis and increases the activity of the β-D-galactopyranoside base. The MUG agent which is a fluorogenic substrate is an alkyl-umbelliferyl-β-D-glucuronide, in particular, a 4-methylumbelliferyl-β-D-glucuronide (MUG), which is cleaved by the enzyme β-D-glucuronidase, which is highly specific for E. coli.

The detection of E. coli is determined by measuring fluorometrically in the long-wave UV range, which fluorescence indicates the presence of E. coli and the absence of fluorescence indicates the absence of E. coli in the test sample. The test broth employs a tryptophan concentration to improve the indolyl reaction for additional confirmation of E. coli and increases the sensitivity of detection in combination with the X-GAL and the MUG reaction. In the prior art, a typical broth composition would then include tryptose, sodium chloride, sorbitol for sugar fermentation, tryptophan, di-potassium hydrogen phosphate and potassium dihydrogen phosphate, lauryl sulfate sodium salt and X-GAL, MUG and IPTG. Thus, the Fluorocult® test permits the determination of the presence or absence of total coliform bacteria, Esherchia, Enterobacter, Klebsiella and Citrobacter as well as E. coli bacteria.

The Fluorocult® LMX Broth in use provides a single strength preparation which is a dehydrated culture medium which is then added to water and subsequently poured into a test tube or test container and autoclaved for 15 minutes at 121° C. Ideally, the LMX Broth should have a pH of 6.8±0.1 at 25° C., and the prepared broth is generally clear and either colorless or slightly yellow. The test sample is added to the prepared broth and incubation is carried out for 24 hours, and in some cases 48 hours, at 35° C. to 37° C. The presence of coliforms is determined by the broth turning blue-green due to the X-GAL reaction while E. coli is detected by measuring the fluorescence which is represented by a light blue fluorescence in the broth. The presence of E. coli may also be confirmed by covering the culture with KOVACS indole reagent, and the presence of E. coli detected by a cherry red color appearing in the reagent, later after one or two minutes, to confirm the presence of E. coli if desired.

None of the cited references are suitable to determine bacteria quantitatively in a large volume of a sample, for example, about 10 ml to 500 ml as in water samples. In order to enumerate bacteria in large sample volumes, e.g. over 10 ml, the sample needs to be filtered through a 0.22–0.45 μm filter or to use multiwell plates.

The filtration technique is the standard technique being used by regulatory agencies and microbiological analytical labs to numerate coliforms in 100 ml samples. Sample filtration with a 0.45 μm filter is done first to recover bacteria from 10 ml to 300 ml water or extraction solution (from particulate food or soil sample) and then cultivate the filter (with the bacteria) on an agar plate with growth media, such as the LMX Fluorocult® or conventional media for coliforms, such as the M-endo agar. This technique needs a sterile filtration assembly, a microbiological hood to perform the filtration and preparation of agar plates. It is laborious and needs a laboratory support, e.g. autoclave, hood and vacuum system for filtration. Common problems encountered with this filtration technique are from small particulates that block the filter, such as silt, dust, rust or other suspended particulates.

Another method is using specific antibodies immobilized to plastic beads or magnetic beads for specific recovery of target bacteria, followed by cultivation of the beads in growth media or selective growth media. This antibody method is expensive and again requires work under sterile conditions and needs highly trained laboratory personnel.

A metabolic identification method is also common and used by microbiological labs and commercial companies for identification of thousands of microorganisms. This method requires enrichments and purification of cultures (a single colony), and it is a laborious, multistep procedure which can take 48 to 96 hours for identification of individual bacteria. It has been reported by Biolog, Inc. of Hayward, Calif. that over 1,100 species can be identified by metabolic tests using specific enzymes and substrates utilization. However, the method is expensive and requires highly trained and skilled laboratory personnel.

Another method known as the Colilert™ (a trademark of Idexx Laboratories, Inc. of Westbrook, Me.) method uses substrate technology of an Idexx Quanti-Tray for coliform enumeration in 100 ml water samples. However, this method which is routinely used by the biotechnology industry for isolation of bacterial or transformed cells is costly, and in the specific case of the Colilert™ method requires a heat sealing system. Numeration at the 25–100 cfu becomes a problem as multiple bacteria can grow in a single cell, and a complex mathematical model is used to correlate the visual results with the actual count (Most Probable Number statistical model—MPN). The Quanti-Tray sealer required for this operation can also become a source of cross contamination. This method is described and claimed in WO95/23026, published Aug. 31, 1995.

It is desirable to provide a new and improved bacteria, test particularly for coliform/*E. coli* that is simple to be performed by the layman, without laboratory equipment and still gives qualitative as well as quantitative results in a short period of time. For example, a test can be performed at 35° C. to 45° C. for 16–24 hours (incubator required) or at a lower temperature of 20° C. to 30° C. for 48–72 hours.

It is desirable to provide an improved MUG test wherein the MUG test either for total coliform bacteria alone or *E. coli*, or a combination thereof, may be rapidly and effectively, not only qualitatively, but quantitatively, determined.

SUMMARY OF THE INVENTION

The invention relates to a qualitative-quantitative test kit and method for microorganisms, and in particular, concerns an improved MUG qualitative-quantitative test kit and method for the determination of total coliforms and/or *E. coli* particularly suitable in large sample volumes, such as 10 ml to 500 ml water samples.

The invention concerns a test method for the quantitative determination of coliform bacteria in a sample, which test method comprises combining in a presterilized container a test sample, water where the test sample does not comprise or constitute water, and a test composition. The test composition comprises a sterile, dried or concentrate growth nutrient medium for the bacteria, and includes a first agent which is cleaved by enzymes in the coliform bacteria to produce and indicate by the presence of a visual color change from the cleavage of the first agent, the presence in the test sample of coliform bacteria. The method includes observing the visual color, or absence in change thereof, to determine the qualitative presence of the coliform bacteria in the test sample.

The improvement in the test method and system comprises adding to the test container prior to incubation a gelling agent which in situ with the water, test sample and the test composition provides a transparent, gel-like or semi-solid broth or cultivation medium, so as to provide an effective incubation environment which restricts bacteria mobility in the environment, but provides nutrients and indicative substrates for the growth of distinct colonies of bacteria and production of the identified color metabolites throughout the gel-like broth or medium. The coliform bacteria colonies form colonies of a visible color; and may be enumerated or quantitatively counted by the visible color of the coliform bacteria colonies to determine the quantitative amount of coliform bacteria in the test sample.

In the LMX media, the reaction of the coloring agent produces a blue-green color in the incubated test broth which indicates the presence of total coliform bacteria, and a total light-blue fluorescent color for the indication of the presence of *E. coli*. These are only qualitative tests. To provide a quantitative assay with this media, the water needs to be filtered and then incubate the filter with solid agar media in a plate. It has been found that the determination of coliform bacteria and/or *E. coli*, or preferably both, particularly with water samples, may be quantitatively determined by employing a gelling agent in the broth, either separately or incorporated into the test composition and admixed with the test sample, which test sample is either a water sample or may have water separately added. The presence of a gelling agent provides for, after admixing and prior to incubation, the rapid increase in the viscosity of the resulting broth to form a jelly-viscous, gelatin or jelly-like, semi-solid broth or medium throughout incubation entrapping individual bacteria and each multiplying as a separate, distinct colony in the broth or medium. The total coliform bacteria and the *E. coli* which are present in the test sample are separately grown throughout the depth of the gel-like broth creating distinct colonies for the actual quantitative counting of the coliform bacteria, which has a blue-green color, or an actual counting of the *E. coli* with a fluorescent meter may be carried out to arrive at both a qualitative and a quantitative determination of the total coliform and *E. coli* in the test sample.

A wide variety of gelling agents may be employed in connection with the invention to provide for the formation in situ of a generally transparent, gel-like consistency in the incubated material in the container, which gelling agent should not substantially or functionally affect the growth of the bacteria during incubation or have any adverse affect on any of the ingredients or the test results. The agent may be employed as a liquid or a powder, alone or in various combinations, preferably a powder-type material, either as a single or a multiple ingredient which reacts or polymerizes upon contact with water to create a semi-solid matrix, so that it may be added to a dehydrated culture medium, that is, to a test composition with a color agent that changes from colorless or other distinct color to a different color, and then is added directly to a water or water-containing sample. The gelling agent should be transparent or relatively colorless, so as not to affect any coloration in the incubated broth, which would interfere with the quantitative counting of the total coliform bacteria and/or *E. coli* in the test sample.

In one embodiment, the gelling agent may be a single component which is added to provide a rapid thickening in the broth without any reaction, for example, but not limited to:

a) a carboxymethyl cellulose, modified starch, polyvinyl alcohol and derivatives and pectin;

b) 1% to 5% by weight of the medium of an alginate cross-linked or reacted with a water insoluble metal ion, like calcium ions;

c) 1% to 5% carrageenans (biopolymers of D-galactose and anhydro galactose) dissolved in buffered water containing sodium salt particles, such a sodium carbonate, the sodium slowly dissolves and cross-links the carrageenan to create a gel and entrap the bacteria; and d) 1% to 5% chitozan (biopolymer of glucosamine, deacetylated chitin) dissolved in buffered water with a pH of 6 and solidified by cross-linking with metaphosphate or tripolyphosphate.

The gelling agent may be added for an in situ reaction or a cross-linking carried out to provide for a gelation of the broth. The gelation time typically should be such that the gelation occurs shortly after admixing the test sample and prior to or during the early stages of the incubation, such as for example, from zero to three hours after admixing, for example, gelation starting thirty minutes to one hour after admixing of the components making up the broth to be incubated with the test sample. The amount of the gelling agent may vary as desired, sufficient added only to provide for the desired gel-like or jelly consistency of the broth. Without wishing to be bound by any particular concentration level, it has been found for example that gelling agents in an amount as low as 0.1 gm to for example up to 10.0 gm/100 ml of broth or more, would be suitable say for example from 0.5 gm to 5.0 gm/100 ml.

Generally, the gelling agent forms the dispersed phase, in water and the water in the test sample forms a continuous phase in the gel broth. Water soluble gelling agents which would be suitable for the gelling agent and employed in the practice of the invention may also include, but not be limited to: collagen and collagen derivatives, such as hydrolysis products of collagen; hydrocolloids derived from natural or synthetic materials, such as alginates, which may be used alone, or alginic acid used alone in an in situ reaction with various metal salts to form an in situ gel-like consistency, such as for example, the reaction of alginic acid with a metal salt, such as calcium, barium, magnesium or other salts to react with a water soluble sodium or potassium alginates to form a gel-like consistency in the broth.

The gelling agent may, for example, include polyvinyl-type compounds, such as polyvinyl alcohol and its derivatives, and vinyl carboxylic-type compounds, such as vinyl acetate, and other type compounds which are known as thickening agents and gelling agents. The gelling agent should require no preheating or dissolution of the gelling agent, as in the case of an agar medium, and rapid gelling or polymerization at room temperature, e.g. 15° C. to 45° C., should occur. In the selection of suitable gelling agents or combinations, polymers toxic to the bacteria or which require organic solvents or which are hydrolyzed by the bacteria normally should be avoided. Other suitable gelling agents may include pectins and derivatives of pectin-type compounds which are suitable thickening or gelling agents and which increase viscosity when admixed with water-containing compositions and includes starches, gums, resins and natural products, like carboxycellulose derivatives, such as carboxymethyl cellulose, and would include silicates, and particularly colloidal silicates which may form thickening and gel-type consistency in water-containing materials.

The test samples employed may be derived from a wide of variety of sources and include food, water, body fluids, such as urine, meat and milk. Where the test sample does not include water, water may be separately added to the dehydrated or powdered test composition when admixed with the test sample to form the broth for incubation.

The invention will be described for the purposes of illustration only in connection with the determination of total coliform bacteria and *E. coli* bacteria in an improved LMX Fluorocult® media employing a water sample. However, it is recognized that the test sample may be derived from a wide variety of sources, and that water can may be separately added to provide a gelling agent with the desired gel-like consistency to provide for the separate formation of the coliform bacteria and *E. coli* bacteria in the incubated broth.

The invention will be described for the purposes of illustration only in connection with certain fluorogenic agents, that is, the MUG agent, as well the coloring agent which is suitable for the detection of the total coliform bacteria and to provide for a blue-green color. However, it is recognized that now or in the future various or additional or new and improved agents may be substituted for these agents for detection of total coliform bacteria and *E. coli* bacteria, or other microorganisms in the test sample that employ the essence of the present invention.

The test kit and method provide a rapid coliform specific test with the results appearing overnight as a visible, distinct blue-green color for a positive sample of total coliform and is designed to provide live coliforms in 100 ml of water according to current Environmental Protection Agency (EPA) requirements for drinking water. The agent may be a test composition containing a dehydrated, powdered culture medium as hereinafter described and containing the gelling agent therein sufficient to provide a slow gel prior to or early in the incubation, typically within the first hour or so of incubation. The equipment required is the employment of a dehydrated test reagent and a long-wave UV light for the detection of any fluorescence zone by the *E. coli*, as well as an incubator operated at 37° C., ±2° C. No fluorescent metering device is required, since the observation may be carried out visually in a shaded area or in the dark using a portable, long-wave lamp.

It is recognized that there are new fluorgenic and chromogenic substrates for glucoronidase which could provide identification of *E. coli* with different color or change in color. For example, if *E. coli* is the main target, using X-glucuronide will result in blue colonies for *E. coli* only and green or blue fluorescent substrate for galactosidase can be used to confirm the general coliforms (see example DetectaGene™ green or blue from Molecular Probe, Inc. of Eugene, Oreg.). Also presently available is ImaGene™ Red for red staining of bacteria with either galactosidase or glucuronidase activities from Molecular Probe, Inc. supra. Thus, the media identification substrate to be used can vary and be formulated according to the priority target bacteria. Other bacteria similar to coliforms could be identified by including other metabolic substrates in the media (for example, the lactic acid bacteria.

In operation, the test kit and test method require a test container, typically, for example, but not limited to a transparent, flexible, throwaway, plastic, sealable bag which contains the dehydrated test composition. The fingers are to be used to break up any possible clumps in the dehydrated reagent in the bag, and the bag is labeled in connection with the particular test. The bag is unsealed, and a defined amount, such as for example, 100 ml of the water sample is then poured in to the bag. As much air as possible is then removed from the bag, and the bag is then closed tightly by folding tightly, for example with a wire strip or other sealing means, to form a water tight seal. With the bag closed, the user employs his fingers to knead or to break up any clumps larger than around 5 mm and to thoroughly mix the reagent medium by shaking the bag from side to side, for example from 10 to 35 seconds, and to make sure that no dry powder remains within the bag of the test container. The bag with the dry medium and the water test sample with the bag sealed is then placed on its side and incubated after being patted flat with the incubation at 37° C., ±2° C., for at least 16 hours or up to 24 hours.

The E*Colite™ (a trademark of Charm Sciences, Inc.) test kit of the invention would include a dried, powdered test medium composition in the bag comprising for example tryptose, sodium chloride, sorbitol, tryptophan, di-potassium hydrogen phosphate, potassium dihydrogen phosphate, lauryl sulfate sodium salt, X-GAL, MUG and IPTG, and a gelling agent which comprises a water soluble alginate salt, such as sodium alginate, and a calcium salt, like calcium carbonate, for use with a large volume water sample to be tested.

The media bag can be divided into two separate chambers by a clip or divider or heat seal line to form a sample collecting chamber and the media chamber. This will have the advantage that the water sample can be treated with thiosulfate to neutralize chlorine or bromine or other oxidants in the sample that could interfere with the growth. The thiosulfate is an important treatment recommended by the EPA. The sample can be transported to the laboratory or incubation place where the divider will be removed and the water sample in the collecting chamber will be allowed to mix with the nutrients, indicator and gelling agent in the media chamber. The use of a ColiGel™ (a trademark of Charm Sciences, Inc. of Malden, Mass.) bag comes with both collection and incubation chambers sterile and test ready and no transfer or filtration or sealing procedures are required. Exposure of the sample to cross contamination is eliminated. The only exposure of the sample will be at the site of collection. Gelation occurs spontaneously upon mixing with water at room temperature (10° C. to 50° C.), and no heating, such as in agar preparation, is needed thereby avoiding the chance of excessive heating which might kill target bacteria in the sample. The formation of the gel also reduces accidental contamination as the bacteria are entrapped in the gel phase which is easily contained. The bag can be easily disposed of in regular trash after heat treatment, such as boiling in water for ten minutes.

After incubation, if the interpretation and results is a negative interpretation and results, that is, the absence of coliform bacteria, would be indicated by no color change from yellow in a turbid medium with no distinct blue-green color change seen. A positive result indicating the qualitative presence of coliforms in the test sample would be separate and distinctive blue-green color spots that formed in the gel-created media. The number of blue-green spots show relative contamination levels per 100 ml of water, that is, a quantitative or semi-quantitative test for the total coliform present. If after 16 hours incubation, the color is inconclusive, that is, for example, weak blue-green color spots, the incubation may be continued up to 24 hours or more and the incubator results again examined. The detection of E. coli positive samples is carried out by incubating the bag for an additional 16 hours, then observing the bag under long-wave UV light (366 nm) for the indication of a light blue fluorescent zone around the blue-green spots which indicates the presence of E. coli and permits the detection of the semi-quantitative amount of E. coli by employing a fluorescent meter against a standard curve. Typically, following the test of all samples, positive and negative, the sample broth should then be boiled in water for ten minutes or autoclaved before disposal. As collection and incubation containers and all media and indicators are sterile, no sterile conditions, like a microbiological hood or an autoclave, are required.

The test kit and method will be described in particular reference to certain illustrated examples; however, it is recognized that those people skilled in the art may make various modifications, changes, improvements and additions to the illustrated embodiments without departing from the spirit and scope of the invention as described.

BRIEF DESCRIPTION OF THE DRAWING

The drawing is the schematic illustration of the test kit and method of the invention.

DESCRIPTION OF THE EMBODIMENTS

The E*Colite™ test kit is a quantitative test of the simultaneous determination of total coliforms and E. coli in water. It is equivalent in performance to the standard membrane filter technique. The test uses specific enzyme inducers in a semi-selective medium to detect the presence of coliforms.

The test medium contains a slow polymerizing component which restricts mobility of bacteria. Thus, each bacteria creates distinguishable colonies for enumeration.

A coliform colony is positively identified based on the formation of a visible and distinctive blue or green color, the product of β-galactosidase activity. E. coli colonies can be further confirmed based on the formation of a zone of fluorescence around the blue/green colonies, the product of β-glucuronidase activity.

The test kit contains ready-to-use sterile medium packaged in a Whirl Pak bag (also available in 2-compartment bags). The upper compartment is for sample collection and treatment with thiosulfate to reduce the effect of chlorine or bromine. The second compartment contains the nutrient and enzyme substrates for the growth and identification of coliforms. The test procedure does not require work under aseptic conditions, filtration or any other sample preparation.

The method is applicable to drinking water, bottled water, ground water, recreation water, surface water and other waters, for the purpose of detection and enumeration of coliforms and/or E. coli at 1-300 cfu per 100 ml range. The test method and procedure are illustrated in the drawing which is self-explanatory. A flexible, transparent, plastic, sealable bag containing sterilized medium with polymerization agent is used. A sample of 100 ml of water (or 300 ml in the 300 ml kit) is added to the bag. The bag is sealed, and the medium is rehydrated with a short kneading and mixing. The bag is laid flat and incubated for 16 to 24 hours at 37° C. Bags are removed from the incubator and are ready for observation and counting of blue/green coliform colonies. Fluorescence around E. coli colonies may be identified with illumination with a UV lamp (366 nm) after 24–48 hours of incubation.

The definitions of the test are:

Coliform and E. coli: negative—No blue/green spots appear in yellow gel after 24 hours.

Coliform: positive—Blue/green spots appear in yellow gel after 16–24 hours.

E. coli: positive—Fluorescent blue/green colonies under UV light after 24–48 hours of incubation at 37° C.

Toxic Material—Seven different industrial disinfectants were tested for interference in the test method.

Soil Particulate—Various soils from light sand to heavy (clay) soil and commercial compost were evaluated for interference in the test. Suspensions were made by adding soil to water at 0.5 and 1 gram per 100 ml and autoclaved for 10 minutes at 121° C. After autoclaving, samples were inoculated with E. coli (ATCC 11775) at 1–10 cfu/100 ml.

All samples (sterile control and inoculated) were incubated for 20 hours at 37° C.

Results indicate the soil had no interference in development, though initial sample color was changed from yellow to brown. Because count is determined by blue/green spots, the initial sample color is not troublesome. All negative samples were negative with clear yellow color. All inoculated samples were positive with blue/green spots. Similarly, fluorescence was not affected by the presence of the soils.

Non-target Organisms—A blind study was conducted in house using sterile bottled water to demonstrate the interference of non-target bacteria in the test. Thirty sterile waters, thirty waters with 10 various non-target strains and thirty waters contaminated with various coliforms at 1–20 cfu level were randomly coded. The inoculum level was quantitated with 3M coliform plates, and selected samples were also quantified by the membrane filter technique. The results demonstrate no false positive in the thirty negative samples, and no false positive in the thirty non-target samples. This is better than 90% selection with 95% confidence and compares to other standard methods. The membrane filtration technique had 0/10 false positive in the negative samples, but had one false positive in the non-coliform bacteria (presumably from carry over from earlier tested samples on the same filter device).

Good laboratory practices should be observed although aseptic conditions are not required. The polymerized medium greatly reduces the risk of laboratory contamination or air contamination. However, after incubation and recording the results, sample bags should be boiled for ten minutes or autoclaved before disposal.

The instrumentation, equipment and supplies required are:

37(±2)° C. incubator

A tray for samples is recommended.

A long wave length ultraviolet lamp (366 nm) is required for *E. coli* confirmation.

The test kit contains:

a) semi-selective medium, enriched with tryptose and sorbitol as main nutrient sources to support growth of coliforms and *E. coli*.

b) specific inducers and substrates for galactisidase (5-Bromo-4-chloro-3-indolyl-β- D-galactoside (X-GAL)) and Glucuronidase (4-Methylumbelliferyl-β-D-glucuronide (MUG))

c) biodegradable polymerizing agent in ready-to-use WHIRL-PAK® (a registered trademark of Nasco Industries, Inc., Ft. Atkinson, Wis.) bag d) sodium thiosulfate (10 mg) is also included in the medium for neutralization of oxidizers such as chloride.

A standard positive enzyme is supplied separately and contains galactosidase or glucuronidase to demonstrate proper blue/green color development of coliforms and fluorescence development of *E. coli*.

Test kit reagents are stable for at least one year at room temperature. Standard reference enzymes are stable for one year at 4° C.

Sample Collection, Dechlorination, Preservation, Shipment and Storage

As indicated, sodium thiosulfate is optionally included in the medium. A sample volume of 105±5 ml water with air space is collected as directed in standard methods or collected directly in the bag (double compartment option) and transported to the lab for incubation as suggested. With the double compartment bags, the sample is collected in the upper compartment and treated with thiosulfate. Upon arrival to the lab, the plastic divider is removed, and the water sample is reconstituted with the media in the lower compartment. Samples collected in the upper compartment or other containers should be refrigerated (2° C. to 8° C.) until transferred to the testing location and reconstituted with the media. Sample containers should be as specified in Standard Methods.

Test Method Performance Characteristics (Sensitivity, Specificity, Recovery and Precision)

A preliminary study using the same growth medium composition, devoid only of the gelling agent component, indicates detection of the following bacteria with better than 95% confidence as positive for coliform:

*Esherchia coli* sp. (40 strains, all positive)

Enterobacter spp. (8 strains, all positive)

Citrobacter spp. (6 strains, all positive)

Klebsiella spp. (7 strains, all positive)

Other groups detected at less than 90%:

Serratia spp. (from 6 strains, 5 were positive)

Shigella spp. (from 3 strains, 2 were positive)

Hafnia spp. (from 2 strains, 1 was positive)

Forty seven other strains, all non-coliform, were tested negative.

A blind coded study was conducted to demonstrate the performance and selectivity of the test method. The samples include:

30 samples containing sterile waters 30 samples inoculated with 10 non-coliform strains 30 samples inoculated with 3 *E. coli* spp., 3 Enterobacter spp., 2 Citrobacter spp. and 2 Serratia spp. (Tables 1–2)

For the coliform preparation, inoculum was targeting levels of 1–20 cfu/100 ml. Fresh cultures were standardized at 585 nm at 0.1 O.D., and then diluted to 10–7. This was used as a stock inoculum for making the samples in PBS, while for the non-coliforms, level 10–4 dilution was used as a stock inoculum for making up the samples. One milliliter of each stock inoculum was quantitatively estimated with Petrofilm™ (a trademark of the 3M Company) 3M Coliform Count Plates. Sterile water samples of 100 ml were inoculated with 1 ml of bacterial stock. Samples were tested by the E*Colite test and the standard membrane filtration technique using M-endo agar.

The results demonstrate no false positive in the thirty negative samples, and no false positive in the thirty non-coliform samples (Table 1–2). This is better than 90% selection with 95% confidence and compares to other standard methods.

All coliforms were tested positive. From the two strains of Serratia (soil coliform), one was tested positive (2 out of 3 samples) and one was negative. The three *E. coli* strains had fluorescence and were positively identified as *E. coli*. The results demonstrated good sensitivity for the Charm C/E test. The membrane filtration technique gave low recovery of bacteria in this study and was attributed to leakage in the filtration assembly. An additional experiment was conducted to access the correlation between E*Colite and the membrane filter technique.

An in-house study was designed to estimate the limit of detection of the test kit with bacteria levels of 1–10 cfu/100 ml. Various strains of *E. coli* and other coliforms were used with dilutions to bring the total bacteria to approximately 1 cfu/ml or below. The inoculum was tested with the Petrofilm™ 3M Coliform Count plates. The results clearly show detection sensitivity at 1 cfu of target bacteria in 100 ml.

In another series of tests, *E. coli* (ATCC 121775) was used to evaluate the quantitative aspect of the test kit, and the correlation with the membrane filter technique. Concentration levels of 1 to 200 cfu/ml were used to generate a correlation between the standard filtration technique and the E*Colite test kit (Table 3). A Petrofilm™ 3M Coliform Count plate was used for inoculum numeration. The regression coefficient of the test kit versus the standard filtration technique was 0.969, and versus the Petrofilm™ 3M, it was R=0.983. The regression analysis gave a y constant close to 1, indicating the methods have similar detection limits at about 1 cfu/ml.

The samples are totally contained in a solidified medium. The polymer used as a gelling reagent is a carbohydrate base, food grade, and fully biodegradable. Use of a plastic Whirl Pak bag eliminates any glassware handling and makes it a pure, biodegradable test. Samples should be autoclaved or boiled after use and discarded in regular trash.

The drawing illustrates and describes the test kit and method for the qualitative determination of total coliform and *E. coli* in a water sample.

The test composition employed in dried, powdered form in each flexible bag for use with 100 ml of a test water sample was:

| | |
|---|---|
| Tryptose | 0.5 g |
| Sodium chloride | 0.5 g |
| Sorbitol | 0.1 g |
| Tryptophan | 0.1 g |
| Di-potassium hydrogen phosphate | 0.27 g |
| Potassium dihydrogen phosphate | 0.2 g |
| Lauryl sulfate sodium salt | 0.01 g |
| X-GAL | 0.008 g |
| MUG | 0.005 g |
| IPTG | 0.01 g |
| Gelling Agent | |
| Sodium alginate | 3.0 g |
| Calcium carbonate | 0.8 g |
| Total per bag/100 ml water sample | 6.503 g |

Comparative, quantitative test data of the test results employed in the test kit (E*Colite™) and method with the standard filter and Inoculum by 3M with various bacteria are summarized in the following tables:

TABLE 1

After 20 hrs at 37° C. Per 100 ml water

| | | | Inoculum by 3M | | E*Colite | | Standard Filter | |
|---|---|---|---|---|---|---|---|---|
| No Microorganism | ATCC | Code # | coliform cfu (total cfu) | Gas Formation Around Colony | coliform cfu | E. coli Fluorescence | total cfu | coliform cfu* |
| 1 *E. coli* | 10536 | 28 | 13 | + | 12 | Yes | 3 | 3 |
| 2 *E. coli* | 11775 | 58 | 10 | + | 23 | Yes | 9 | 9 |
| 3 *E. coli* | 25922 | 100 | 11 | + | 4 | Yes | 3 | 3 |
| 4 Enterobacter | 13045 | 69 | 16 | + | 22 | No | 35 | 1 |
| 5 Enterobacter | 49701 | 30 | 15 | + | 8 | No | 2 | 0 |
| 6 Enterobacter | 13047 | 53 | 22 | + | 10 | No | 3 | 0 |
| 7 Serratia | 13880 | 44 | 8 | No | 0 | No | 17 | 0 |
| 8 Serratia | 33105 | 64 | 9 | No | 2 | No | 8 | 0 |
| 9 Citrobacter | 6750 | 73 | 20 | + | 12 | No | 7 | 7 |
| 10 Citrobacter | 8090 | 60 | 15 | + | 2 | No | 25 | 25 |
| 11 *B. cereus* | 11778 | 66 | 0 (700) | No | 0 | No | 1 | 0 |
| 12 *B. thuringiensis* | 35646 | 56 | 0 (400) | No | 0 | No | TNTC | 0 |
| 13 *Ps. aeroginosa* | 27853 | 94 | 0 (>1000) | No | 0 | No | 0 | 0 |
| 14 *Ps. putida* | 17484 | 76 | 0 (250) | No | 0 | No | 2 | 1 |
| 15 Enterococcus | 29212 | 92 | 0 (800) | No | 0 | No | | |
| 16 *E. coli* | 10536 | 13 | 13 | + | 17 | Yes | | |
| 17 *E. coli* | 11775 | 31 | 10 | + | 15 | Yes | | |
| 18 *E. coli* | 25922 | 47 | 11 | + | 14 | Yes | | |
| 19 Enterobacter | 13045 | 11 | 16 | + | 17 | No | | |
| 20 Enterobacter | 49701 | 39 | 15 | + | 14 | No | | |
| 21 Enterobacter | 13047 | 43 | 22 | + | 13 | No | | |
| 22 Serratia | 13880 | 54 | 8 | No | 0 | No | | |
| 23 Serratia | 33105 | 35 | 9 | + | 0 | No | | |
| 24 Citrobacter | 6750 | 25 | 20 | + | 11 | No | | |
| 25 Citrobacter | 8090 | 65 | 15 | + | 14 | No | | |
| 26 *B. careus* | 11778 | 29 | 0 (700) | No | 0 | No | | |
| 27 *B. thuringiensis* | 35646 | 15 | 0 (400) | No | 0 | No | | |
| 28 *Ps. aeroginosa* | 27853 | 67 | 0 (>1000) | No | 0 | No | | |
| 29 *Ps. putida* | 17484 | 33 | 0 (250) | No | 0 | No | | |
| 30 Enterococcus | 29212 | 68 | 0 (800) | No | 0 | No | | |

*shainy colonies
NT - not tested
NG - No colonies observed
(Total cfu) - 3M aerobic plate

TABLE 2

| No | Microorganism | ATCC | code # | Inoculum by 3M-cfu coliform cfu (aerobic) | Gas Formation Around Colony | E*Colite coliform cfu | E. coli Fluorescence | Standard Filter total cfu | coliform cfu* |
|---|---|---|---|---|---|---|---|---|---|
| 31 | E. coli | 10536 | 41 | 3 | + | 1 | Yes | | |
| 32 | E. coli | 11775 | 95 | 5 | + | 3 | Yes | | |
| 33 | E. coli | 25922 | 59 | 3 | + | 5 | Yes | | |
| 34 | Enterobacter | 13045 | 86 | 8 | + | 5 | No | | |
| 35 | Enterobacter | 49701 | 62 | 5 | + | 3 | No | | |
| 36 | Enterobacter | 13047 | 71 | 7 | + | 6 | No | | |
| 37 | Serratia | 13880 | 61 | 4 | neg | 0 | No | | |
| 38 | Serratia | 33105 | 63 | 2 | neg | 0 | No | | |
| 39 | Citrobactor | 6750 | 77 | 10 | + | 4 | No | | |
| 40 | Citrobactor | 8090 | 97 | 7 | + | 3 | No | | |
| 41 | B. cereus | 11778 | 1 | 0 (700) | NA | 0 | No | | |
| 42 | B. thuringiensis | 35646 | 84 | 0 (400) | NA | 0 | No | | |
| 43 | Ps. aeriginosa | 27853 | 38 | 0 (>1000) | NA | 0 | No | | |
| 44 | Ps. putida | 17484 | 6 | 0 (250) | NA | 0 | No | | |
| 45 | Enterococcus | 29212 | 55 | 0 (800) | NA | 0 | No | | |
| 46 | Baker yeast | | 21 | 0 (27) | NA | 0 | No | | |
| 47 | B. catarhallis | 25238 | 36 | 0 (195) | NA | 0 | No | | |
| 48 | Lactococcus | 11603 | 82 | NG | NA | 0 | No | | |
| 49 | B. catarhallis | 25238 | 27 | 0 (195) | NA | 0 | No | | |
| 50 | Baker yeast | | 22 | 0 (27) | NA | 0 | No | | |
| 51 | St. aureus | 12598 | 90 | 0 (40) | NA | 0 | No | | |
| 52 | B. subtilis | 6633 | 96 | 0 (96) | NA | 0 | No | | |
| 53 | B. subtilis | 6633 | 46 | 0 (96) | NA | 0 | No | | |
| 54 | Lactococcus | 11603 | 78 | NG | NA | 0 | No | | |
| 55 | St. aureus | | 32 | 0 (40) | NA | 0 | No | | |
| 56 | Lactococcus | 11603 | 88 | NG | NA | 0 | No | | |
| 57 | Baker yeast | 7468 | 24 | 0 (27) | NA | 0 | No | | |
| 58 | B. catarhallis | 25238 | 19 | 0 (195) | NA | 0 | No | | |
| 59 | B. subtilis | 6633 | 4 | 0 (96) | NA | 0 | No | | |
| 60 | St. aureus | 12598 | 23 | 0 (40) | NA | 0 | No | | |

*shainy colonies
NT - not tested
NG - No colonies observed
(aerobic) - 3M aerobic plate

TABLE 3

Numeration of E. coli by the ColiGel vs. Standard Filter method
An Example for E. coli (ATCC #11775)

| Inoculum 3m Total cfu | LMX Fluoro-cult Coliform blue neg/pos | LMX Fluoro-cult E. coli Fluor. neg/pos | Charm E*Colite/Coligel Coliform blue cfu | Charm E*Colite/Coligel E. coli fluor cfu | Standard Filter Coliform cfu |
|---|---|---|---|---|---|
| 0 | neg | neg | 0 | 0 | 0 |
| 0 | neg | neg | 0 | 0 | 0 |
| 0 | neg | neg | 0 | 0 | 0 |
| 0 | neg | neg | 0 | 0 | 0 |
| 0 | neg | neg | 0 | 0 | 0 |
| 0 | neg | neg | 0 | 0 | 0 |
| 8 | pos | pos | 9 | 9 | 6 |
| 7 | pos | pos | 11 | 11 | 12 |
| 8 | pos | pos | 12 | 12 | 10 |
| 8 | pos | pos | 13 | 13 | 10 |
| 8 | pos | pos | 13 | 13 | 9 |
| 16 | pos | pos | 17 | 17 | 23 |
| 16 | pos | pos | 22 | 22 | 25 |
| 54 | pos | pos | 44 | 44 | 48 |
| 54 | pos | pos | 45 | 45 | 50 |
| 48 | pos | pos | 51 | 51 | 61 |
| 105 | pos | pos | 95 | 95 | 109 |
| 105 | pos | pos | 96 | 96 | 100 |
| 126 | pos | pos | 106 | 106 | 140 |
| 121 | pos | pos | 114 | 114 | 137 |
| 105 | pos | pos | 114 | 114 | 103 |
| 120 | pos | pos | 124 | 124 | 129 |
| 128 | pos | pos | 139 | 139 | 124 |
| 154 | pos | pos | 141 | 141 | 177 |
| 168 | pos | pos | 145 | 145 | 176 |
| 169 | pos | pos | 154 | 154 | 185 |
| 163 | pos | pos | 183 | 183 | 179 |

What is claimed is:

1. In a test method for the quantitative determination of bacteria in a sample, which test method comprises:

a) combining in a container a test sample, water where the test sample does not comprise or constitute water, and a test composition, which composition comprises a growth nutrient medium for the bacteria, and a first chromogenic agent which is cleaved by enzymes in the bacteria to produce and to indicate by the presence of a color from the cleavage of the first agent, the presence in the test sample of bacteria; and b) observing the color, or absence thereof, to determine the quantitative presence of the bacteria in the test sample, the improvement which comprises:

i) providing a sterile, flexible, transparent, sealable, plastic test container which includes therein a powdered test composition and a gelling agent in amount to provide in situ with the water or test sample and the test composition a generally transparent gel medium;

ii) adding the test sample or water to said test container;

iii) sealing said test container;

iv) admixing the test sample or water with the powdered test composition and gelling agent in said sealed container to form a generally transparent gel medium;

v) forming the gel medium in said sealed container into a generally flat gel medium layer;

vi) incubating the flat gel medium layer to provide for the growth, if any, of bacteria in said test sample throughout the gel medium layer; and vii) counting the color of the bacteria colonies in the incubated gel layer to determine the quantitative amount of bacteria in the test sample.

2. The method of claim 1 wherein the gelling agent comprises a single component, water soluble material.

3. The method of claim 1 wherein the gelling agent is a powdered gelling agent and incorporated into said powdered test composition.

4. The method of claim 1 wherein the gelling agent comprises two or more ingredients which ingredients react in situ in the test container to form a gel-like media.

5. The method of claim 1 wherein the gelling agent is incorporated in the test composition and comprises an admixture of a water soluble alginate salt and a metal salt, which water soluble alginate and metal salt react in the presence of water to form a metal alginate and to form the gel medium.

6. The method of claim 5 wherein the gelling agent comprises a sodium or potassium alginate, and the metal salt comprises a calcium salt.

7. The method of claim 5 wherein the gelling agent comprises an admixture in the test composition of from about 2 gm/100 ml to 5 gm/100 ml of a water soluble alginate, and about 0.5 gm/100 ml to about 1.0 gm/100 ml of a metal salt to form a water insoluble metal salt alginate.

8. The method of claim 1 wherein the gelling agent comprises from about 0.1 g/100 ml to 10 g/100 ml of the medium.

9. The method of claim 1 wherein said plastic container comprises two chambers separated by a sealing means, and which method includes providing said two chamber container with said first sealed chamber containing said test composition and gelling agent, and introducing the test sample into said second chamber, and removing the sealing means to permit admixing of the test sample, with the test composition and gelling agent in said first chamber.

10. The method of claim 9 wherein said first chamber has a volume sufficient to receive a test sample of from about 100 ml to 500 ml.

11. The method of claim 9 wherein the sealing means comprises a removable clip divider or heat seal divider to form the two chambers, and which method includes removing the clip or heat seal divider to permit admixing of the powdered test composition, gelling agent, and water or test sample.

12. The method of claim 1 which includes forming the gel medium layer without heating.

13. The method of claim 1 which includes sterilizing the sealed test container after counting, and disposing of the sterilized sealed container.

14. The method of claim 13 which includes sterilizing the sealed container by boiling in water or autoclaving.

15. The method of claim 1 wherein the first agent comprises a galactopyranoside and which test composition includes: an amplifying agent to increase the activity of the enzyme synthesis; a second fluorogenic agent which comprises glucuronide; and tryptophan.

16. The method of claim 9 which includes providing a thiosulfate in the first chamber to neutralize oxidants in the test sample introduced into the first chamber.

17. The method of claim 1 which includes selecting a gelling agent which gelling agent provides for the formation of a gel-like medium in about two hours or less after admixing with the test sample.

18. The method of claim 1 which comprises detecting the amount of coliform bacteria or $E.\ coli$, or both, in the test sample.

19. The method of claim 18 which includes incubating the gel medium layer with the use of an incubator at about 35° C. to 45° C. for about 16 to 24 hours or without the use of an incubator at about 20° C. to 30° C. for 48 to 72 hours.

20. The method of claim 1 wherein the test sample comprises a water sample having a volume of 10 ml to 500 ml.

21. The method of claim 18 wherein the first agent provides for a visible blue-green color about the coliform bacteria.

22. The method of claim 18 wherein the first agent comprises a halo-indolyl-$\beta$-D-galactopyranoside.

23. The method of claim 18 wherein the test composition includes an amplifying amount of a thiogalactopyranoside.

24. The method of claim 1 which includes a second agent which comprises an alkyl-umbelliferyl-$\beta$-D-glucuronide (MUG) and wherein the second agent is cleaved by enzymes in $E.\ coli$ bacteria and which second agent indicates by the presence of a fluorescent color, the presence of $E.\ coli$ bacteria in the test sample, and which method includes measuring the fluorescent color to determine quantitatively the amount of $E.\ coli$ bacteria in the test sample.

25. The method of claim 1 wherein the test composition includes tryptophan to increase the sensitivity of the test method.

26. In a test method for the quantitative determination of total coliform bacteria and $E.\ coli$, which test method comprises:

a) combining in a test container a water test sample to be tested for a total coliform bacteria and $E.\ coli$ with a powdered test composition, which powdered test composition comprises a growth nutrient medium for the coliform bacteria, and a first chromogenic agent which is cleaved by an enzyme in the coliform bacteria to produce a color in the resulting broth and to indicate by the presence of the color the presence in the test sample of coliform bacteria, and a second fluorescent agent which is cleaved by an enzyme in the $E.\ coli$ bacteria to indicate by the presence of a fluorescent color the presence of $E.\ coli$ bacteria in the test sample; and b) observing the physical color, or absence thereof, and observing fluorometrically the fluorescent color, or absence thereof, to determine the qualitative presence of total coliform bacteria and $E.\ coli$ bacteria in the sample, the improvement which comprises:

i) providing a water soluble, powdered two component reactable gelling agent in the test composition, which gelling agent reacts in situ in the presence of the water test sample to form a transparent, semisolid gel medium within about two hours of the combining of the water sample and test composition and prior to incubation so as to restrict the mobility of coliform bacteria and $E.\ coli$ formed during incubation;

ii) providing a sterile, sealable, transparent, flexible plastic bag as the test container, the plastic bag divided by a removable divider into a first chamber and a second chamber, the second chamber containing the test composition and the gelling agent;

iii) introducing the water test sample in an amount of from about 10 ml to 500 ml into the first chamber and sealing the first chamber;

iv) removing the divider;

v) admixing the test composition and gelling agent with the water test sample to provide a gel medium containing the test sample;

vii) pressing the sealed plastic bag with the gel medium to form a generally flat transparent gel medium layer in the sealed transparent plastic bag;

viii) incubating the plastic bag with the gel medium layer to provide for the growth of separate colonies of total coliform bacteria in visible color throughout the gel medium layer and to provide a fluorescent zone about colonies of the E. coli bacteria throughout the gel medium layer; and ix) quantitatively measuring the total coliform bacteria by counting the colonies associated with the total coliform bacteria in the gel medium layer, and quantitatively counting with long wave ultraviolet light, the fluorescent zone about the E. coli fluorescent colonies.

27. The method of claim 26 which includes employing a gelling agent of a metal salt alginate.

28. The method of claim 26 wherein the first chamber includes an agent to oxidize halogens in the test sample.

29. The method of claim 26 wherein the first agent comprises a halo-indolyl-β-D-galactopyranoside, the second agent comprises an alkyl-umbelliferyl-β-D-glucuronide, and wherein the test composition includes a thiogalactopyranoside amplifying agent and tryptophan.

30. The method of claim 26 which includes sterilizing the sealed plastic bag after the measuring step and disposing of the sealed sterilized plastic bag and the incubated gel medium therein.

31. A test kit for the qualitative determination of bacteria in a test sample, which test kit comprises:

a) a sterile, sealable, flexible, transparent, plastic bag as a test container and having an opening for the introduction of a test sample, which test sample comprises water or has a water content, and means to seal the opening in the plastic bag after introduction of the test sample;

b) a powdered test composition for admixture with the test sample in the plastic bag, and which test composition comprises:

i) a growth nutrient medium for bacteria;

ii) a first agent which is cleaved by enzymes in the bacteria to produce and to indicate by the presence of a visual color from the cleavage of the first agent the presence in the test sample of bacteria; and iii) a powdered gelling agent in the plastic bag which on admixture in the plastic bag with the test sample and the test composition forms a transparent, gel medium which may be formed into a flat, transparent gel medium layer in the plastic bag prior to incubation to restrict the mobility of the bacteria on growth in the flat gel medium layer on incubation.

32. The test kit of claim 31 wherein the plastic bag includes removable means to divide the bag into a separate test sample collecting chamber to receive the test sample and a separate media chamber containing the powdered test composition and gelling agent.

33. The test kit of claim 32 wherein the sample collecting chamber contains an oxidant agent to neutralize oxidants in the water test sample.

34. The test kit of claim 31 wherein the means to divide comprises a seal line between the said chambers.

35. The test kit of claim 31 wherein the means to divide comprises a plastic clip divider.

36. The test kit of claim 31 wherein the means to seal comprises a wire strip.

37. The test kit of claim 31 wherein the powdered test composition includes as the gelling agent a water soluble alginate and a metal salt which form, in the presence of the water test sample, a metal alginate.

38. The test kit of claim 31 wherein the powdered test composition includes an agent for the detection of E. coli which is cleaved by enzymes in the E. coli to indicate by a fluorescent color the presence of E. coli under ultraviolet light in the test sample.

39. The test kit of claim 32 wherein the plastic bag is arranged and constructed to receive a volume of from about 10 ml to 500 ml of the test sample.

40. The test kit of claim 38 which includes:

a) a means to incubate the sealed plastic bag in a flat condition after admixture of the test sample and the powdered test composition and gelling agent; and b) an ultraviolet light source means to detect E. coli in the test sample.

41. The test kit of claim 22 wherein the test composition comprises: halo-indolyl-β-D-galactopyranoside as a first agent and wherein the second agent comprises an alkyl-umbelliferyl-β-D-glucuronide, and the test composition includes a thiogalactopyranoside amplifying agent and tryptophan.

42. A method of preparing a gel medium layer for use in the determination of bacteria, which method comprises:

a) providing an admixture in a water-containing test sample powdered test composition which comprises: a growth nutrient medium for the bacteria and a chromogenic agent which is cleaved by enzymes in the bacteria to indicate, by the presence of a color from the cleavage of the first agent, the presence in the test sample of bacteria; and a powdered gelling agent admixed in an amount to provide in situ with the water-containing test sample a generally transparent gel medium;

b) adding a water-containing test sample to the admixed powdered test composition and gelling agent to form in situ a generally transparent gel medium; and c) forming the gel medium into a generally flat gel medium layer prior to any incubation of the gel medium.

43. The method of claim 42 which includes carrying out the formation of the gel medium in a container.

44. The method of claim 42 wherein the gelling agent comprises an alginate.

45. The method of claim 42 which includes forming the in situ gel medium without heating and within a period of about two hours.

46. The method of claim 42 wherein the test composition is selected for the determination of coliform bacteria.

47. The gel medium layer produced by the method of claim 42.

* * * * *

UNITED STATES PATENT AND TRADEMARK OFFICE
CERTIFICATE OF CORRECTION

PATENT NO.   :   5,605,812
DATED        :   Feb. 25, 1997
INVENTOR(S)  :   Zomer It is certified that error appears in the above-indentified patent and that said Letters Patent is hereby corrected as shown below:

Column 14, line 63 (claim 1, line 12) delete "quantitative" and insert --qualitative--.

Column 16, line 31 (claim 24, line 4) after "indicates" and before "by" insert --,--.

Column 18, line 28 (claim 41, line 1) delete "22" and insert --31--.

Signed and Sealed this

Thirteenth Day of May, 1997

Attest:

BRUCE LEHMAN

Attesting Officer

Commissioner of Patents and Trademarks